United States Patent
Matvejev et al.

(10) Patent No.: US 10,107,771 B2
(45) Date of Patent: Oct. 23, 2018

(54) SENSOR FOR DIELECTRIC SPECTROSCOPY OF A SAMPLE

(71) Applicants: IMEC VZW, Leuven (BE); Vrije Universiteit Brussel, Brussel (BE)

(72) Inventors: Vladimir Matvejev, Lithuania (BE); Johan Stiens, Bonheiden (BE); Yuchen Zhang, Leuven (BE)

(73) Assignees: IMEC VZW, Leuven (BE); VRIJE UNIVERSITEIT BRUSSEL, Brussels (BE)

( * ) Notice: Subject to any disclaimer, the term of this patent is extended or adjusted under 35 U.S.C. 154(b) by 235 days.

(21) Appl. No.: 15/023,344

(22) PCT Filed: Sep. 17, 2014

(86) PCT No.: PCT/EP2014/069748
§ 371 (c)(1),
(2) Date: Mar. 18, 2016

(87) PCT Pub. No.: WO2015/040037
PCT Pub. Date: Mar. 26, 2015

(65) Prior Publication Data
US 2016/0313269 A1  Oct. 27, 2016

(30) Foreign Application Priority Data
Sep. 18, 2013 (EP) .................... 13184915

(51) Int. Cl.
G01N 17/00 (2006.01)
G01N 27/02 (2006.01)
(Continued)

(52) U.S. Cl.
CPC ....... *G01N 27/026* (2013.01); *G01N 21/3581* (2013.01); *G01N 33/48707* (2013.01); *G01N 2201/08* (2013.01)

(58) Field of Classification Search
CPC ............. G01N 27/026; G01N 21/3581; G01N 33/48707; G01N 2201/08
(Continued)

(56) References Cited

U.S. PATENT DOCUMENTS

2004/0145426 A1* 7/2004 Wu .................. H01P 5/082
333/26
2011/0241802 A1* 10/2011 Joshi .................. H01P 1/219
333/209

FOREIGN PATENT DOCUMENTS

WO    WO99/039008 A1    8/1999

OTHER PUBLICATIONS

Bin Zhu et al. (Inexpensive and easy fabrication of multimode tapered dielectric circular probes at millimeter wave frequencies). vol. 126, 237-254, 2012.*
(Continued)

*Primary Examiner* — Farhana Hoque
(74) *Attorney, Agent, or Firm* — McDonnell Boehnen Hulbert & Berghoff LLP

(57) ABSTRACT

A sensor for dielectric spectroscopy of a sample is disclosed. The sensor comprises a waveguide inductively loaded with a composite dielectric section which comprises a sample holder and a discontinuity separating the sample holder from the waveguide. The electromagnetic impedance of the composite dielectric section varies gradually, at least along the propagation direction of the waveguide, and at least from the onset of the discontinuity towards the sample holder.

20 Claims, 14 Drawing Sheets

(51) Int. Cl.
  *G01N 21/3581* (2014.01)
  *G01N 33/487* (2006.01)
(58) Field of Classification Search
  USPC .................................... 324/601, 633, 700
  See application file for complete search history.

(56) References Cited

OTHER PUBLICATIONS

PCT Search Report and Written Opinion, PCT International Application No. PCT/EP2014/069748, dated Dec. 18, 2014.
Zhu, B. et al., "Inexpensive and Easy Fabrication of Multi-Mode Tapered Dielectric Circular Probes at Millimeter Wave Frequencies", Progress in Electromagnetics Research, vol. 126, Dec. 31, 2012, pp. 237-254.
Matvejev, V. et al., "Label-Free Investigation of Yeast Cell Physiology in Capillary Tubes Sensed by THz Waves", Proceedings ESA Workshop on Millimeter-Wave Technology and Applications, Apr. 1, 2011, 4 pages.
Matvejev, V. et al., "Integrated Waveguide Structure for Highly Sensitive THz Spectroscopy of Nano-Liter Liquids in Capillary Tubes", Progress in Electromagnetics Research, vol. 121, 2011, pp. 89-101.
Communication Pursuant to Article 94(3) EPC, European Patent Application No. 14771833.2, dated Sep. 25, 2017, 4 pages.
Communication Pursuant to Article 94(3) EPC, European Patent Application No. 14771833.2, dated Apr. 5, 2018, 5 pages.

* cited by examiner

SENSOR FOR DIELECTRIC SPECTROSCOPY OF A SAMPLE

CROSS-REFERENCE TO RELATED APPLICATION

The present application is a national stage entry of PCT/EP2014/069748 filed Sep. 17, 2014 which claims priority to European Patent Application No. 13184915.1 filed on Sep. 18, 2013, the contents of each of which are hereby incorporated by reference.

FIELD

The present disclosure relates to sensors for dielectric spectroscopy of samples, in particular to sensors comprising substrate integrated waveguides operating a terahertz frequencies.

BACKGROUND

Millimeter (MM) and TeraHertz (Thz) electromagnetic waves, i.e. waves having a frequency in the range $3 \times 10^{10}$ to $3 \times 10^{11}$ and $10^{11}$ to $10^{13}$ Hz, respectively, can probe various inter- and intra-macromolecular functional properties: biomolecule's and lipid membrane's hydration, binding reactions with other biomolecules, conformational changes and its functioning. This creates new possibilities for real-time, immobilization-free and label-free biosensing of biomolecular entities of different complexity: cells, nucleic acids, proteins, polypeptides, carbohydrates, lipids.

The majority of studies were carried out with specially treated samples in order to overcome the severe attenuation of THz waves by liquids which shadow the biomolecules' response. Pressed pellets, hydrated films and cryogenically frozen samples enable free-space measurements to be carried out on biological samples with a reasonable sensitivity at THz frequencies. A disadvantage of these measurement methods is that the unnatural environment, does not allow investigations of biomolecule's conformational evolution with biological function. Another major drawback with free-space measurements is the necessity for large sample quantities and high-performance equipment such as bright sources or sensitive detectors, which prohibits wide-scale application and commercialization.

Integrated THz sensing approaches have proved to be more sensitive and sample quantity-reducing, but measurements with sufficient hydration still present a challenge. In integrated sensors based on planar transmission lines the sample cannot be loaded at the location of maximum EM field strength, resulting in a large propagation attenuation along the longer transmission line which is required for a longer interaction path length. In the case of a single wire transmission line, the interaction is much stronger. However both planar transmission lines and single wire transmission lines suffer from excessive losses which reduce the measurement sensitivity to dielectric permittivity changes in the sample.

V. Matvejev et al, discloses in "Integrated waveguide structure for highly sensitive THz spectroscopy of nano-liter liquids in capillary tubes", published in "Progress In Electromagnetics Research" 2011, vol. 121, p 89 to 101, a technique for highly sensitive THz liquid spectroscopy, which is suitable for bio-sensing applications. The sensor consisted of integrated low-loss hexagonal cross-section waveguide comprising a squared opening and a commercially available fused silica capillary tube positioned in this opening.

SUMMARY

In a first aspect, a sensor for dielectric spectroscopy of a sample is disclosed, the sensor comprising a waveguide inductively loaded with a composite dielectric section which comprises a sample holder and a discontinuity separating the sample holder from the waveguide, whereby the electromagnetic impedance of the composite dielectric section varies gradually, at least along the propagation direction of the waveguide, at least from the onset of the discontinuity towards the sample holder.

Preferably, the composite dielectric section of this sensor constitutes a dielectric resonator. Preferably this dielectric resonator is configured as a quasi-half wave length resonator. Preferably, the electromagnetic impedance of the composite dielectric section is configured to yield minimal reflection at resonance frequency.

In one embodiment, the discontinuity of the composite dielectric section is an opening.

In one embodiment, the container is a capillary tube. Preferably, this capillary tube extends at least from one side of the composite dielectric section to the opposite side in a direction perpendicular to the propagation direction of the waveguide.

In one embodiment, the composite dielectric section further comprises a electromagnetic impedance tuner. This electromagnetic impedance tuner can be configured for varying the wall thickness of the sample holder, the position of the sample holder in the discontinuity and/or the dimensions of the discontinuity. In the latter the electromagnetic impedance tuner can be a diaphragm. This electromagnetic impedance tuner can comprise a dual chamber holder whereby a first part holds the sample and the second part holds a liquid with tunable composition. The electromagnetic impedance tuner can be configured for varying the dimensions of the composite dielectric section in a direction perpendicular to the propagation direction of the waveguide In one embodiment, the waveguide is a homogeneous waveguide.

In a second aspect, a method for designing a sensor according to the first aspect is disclosed, the method comprises: selecting a frequency band, dimensioning the waveguide in accordance with the selected frequency band, and dimensioning the composite dielectric section as a quasi-half-wave length resonator within the selected frequency band. Preferably, dimensioning the composite dielectric section is dimensioned by dimensioning the sample holder and/or the discontinuity.

In a third aspect, a method for operating a sensor according to first aspect, is disclosed, the method comprising: introducing a sample in the sample holder, and measuring the response of the waveguide. Preferably the sample is a liquid.

In one embodiment, when the sensor comprises a electromagnetic impedance tuner, the method further comprises before introducing the sample, calibrating the sensor by introducing a reference sample in the sample holder and tuning the sensor thereby minimizing the reflection signal at the resonance frequency. Optionally, before calibrating the sensor with the reference sample, the method can further comprises further calibrating the electromagnetic impedance tuner by introducing a calibration element into the sensor and tuning the sensor thereby minimizing the reflection signal at the resonance frequency.

FIGURES

For teaching the present disclosure, some exemplary embodiments are described below in conjunction with the appended figures and figures description.

DESCRIPTION

A sensor for dielectric spectroscopy of a sample is disclosed, the sensor comprising a waveguide inductively loaded with a composite dielectric section which comprises a sample holder and a discontinuity separating the sample holder from the waveguide, whereby the electromagnetic impedance of the composite dielectric section varies gradually, at least along the propagation direction of the waveguide, at least from the onset of the discontinuity towards the sample holder.

This sensor should preferably meet the following requirements. The electromagnetic signal used to analyze the dielectric properties of the sample should be conveyed by the sensor with minimal loss to the volume of the sample. Hereto the electromagnetic properties of at least the composite dielectric section are graded towards the sample. This gradient makes the sensor more robust as the sensitivity of the sensor towards geometrical changes is reduced. The response of the sensor will be less dependent on variations on the dimensions of the discontinuity and/or the sample holder, e.g. due to manufacturing tolerances, or on the exact position of the sample holder in the discontinuity. When the grading is well organized, this can yield additional concentration of the energy of the electromagnetic signal, allowing sampling smaller volumes with improved sensitivity. The volume of the sample should be limited such that the sensor still acts as a low-loss waveguide. The volume limitation is particularly relevant if highly absorbing material, such as aqueous solution, is tested. The sensor is hence designed as a half wavelength resonator whereby the effective dielectric index of the composite dielectric section is graded towards the sample. The sensor configuration allows interrogating materials which volume is much smaller than the waveguide cross-section with a maximum sensitivity and minimum signal loss towards the material under test.

Figure 1:
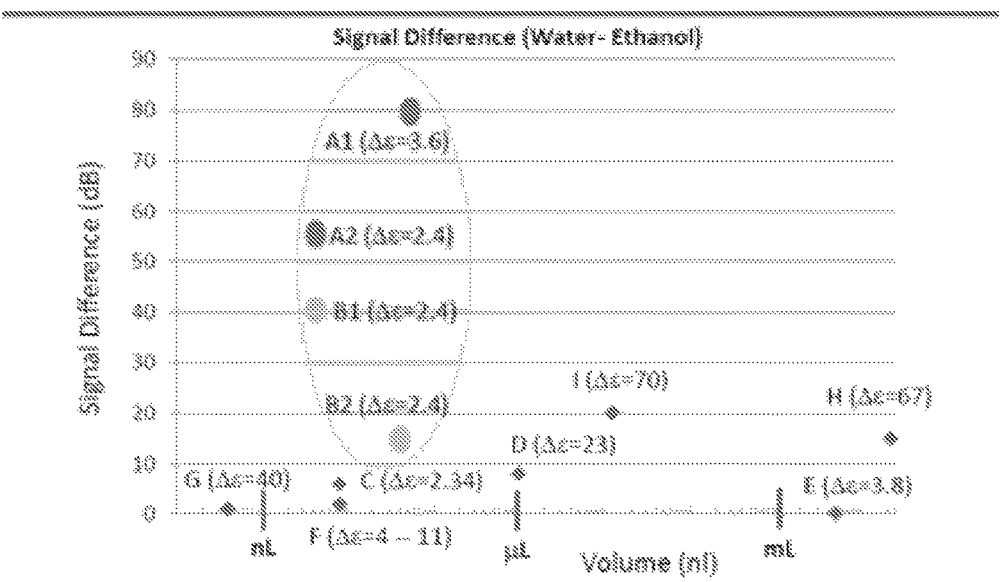
FIG. 1 shows the signal difference between reference sample (water) and sample (ethanol) for various test methods (circle: disclosure, diamond: prior art).

In FIG. 1 the circles refer to a sensor designed according to this disclosure whereby the layout and/or configuration is varied. Results (within the ellipse: green (A) and yellow (B) circles) according to this disclosure are compared with results (C, D, E, F, G, H, I) published in literature. At the nano-liter level the sensitivity of sensors according to this disclosure are still 100 to million times more sensitive than the prior art sensors who operate at micro- or milliliter level. The sensor can be monolithically integrated e.g. in semiconductor material or in a polymer material.

The response of the disclosed sensor is determined by i) the shape and the dimensions of the cross-section of the waveguide, ii) the dimensions of the discontinuity e.g. an opening or slot, in the waveguide, iii) the dimensions and electromagnetic properties of the sample holder e.g. shape, thickness of the wall, inner dimension and outer dimension, height and/or the dielectric permittivity of the material of the sample holder, and iv) the electromagnetic properties and volume of the sample.

Figure 2A:
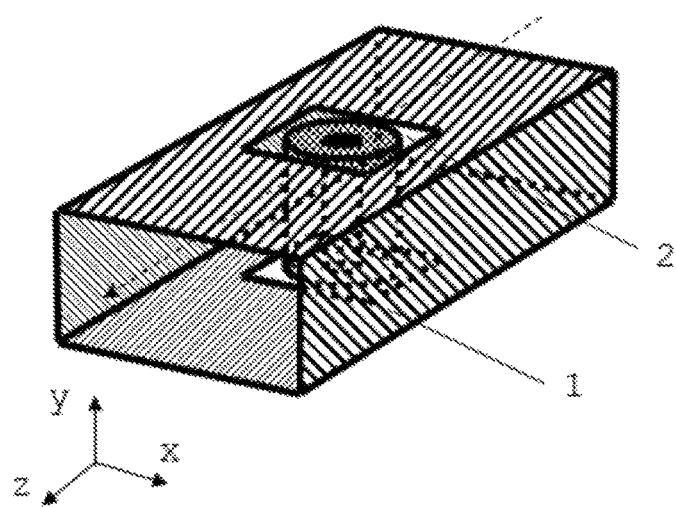
FIG. 2a shows a sample holder within the waveguide whereby the discontinuity overlaps the sample holder.
Figure 2B:
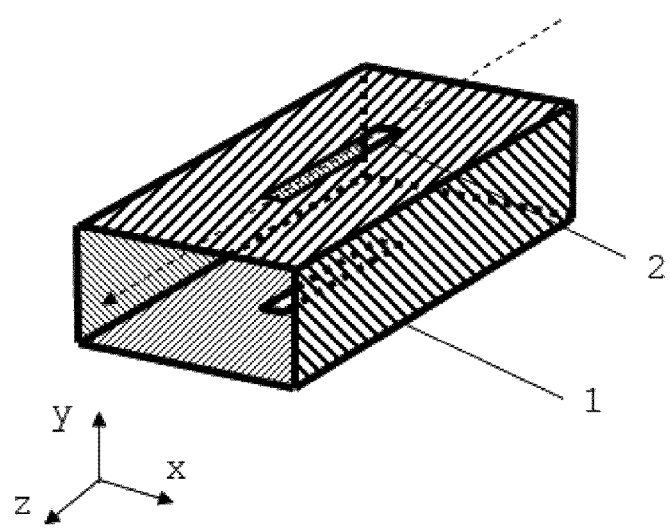
FIG. 2b shows a sample holder within waveguide whereby the sample holder overlaps the opening (slot) (2) in a direction perpendicular to the propagation direction.

If highly absorbing material is used, the volume of the composite dielectric section should be substantially larger than the sample volume. In order to allow easy injection of the sample into the composite dielectric section, the case being into the sample holder, the waveguide should have an opening. This layout and position of such opening or slot (2) is shown in FIGS. 2a and 2b. The transverse opening, i.e. perpendicular to the propagation direction (dotted line) of the waveguide (1), should be smaller than the horizontal cross-section area of the composite dielectric section and larger than a practical minimum inlet for the sample. This discontinuity, here in the form of an opening or slot, allows the excitation of the main resonance as discussed further.

Resonance Mechanisms

During operation, thanks to the layout and configuration of the sensor, constructive interaction between various resonance mechanisms will occur.

A first resonance is this of the composite dielectric section with sample holder containing the sample, but without discontinuity.

In analogy to the propagation constant of the medium, $k=2\pi f\sqrt{\mu\epsilon}$, the cutoff wavenumber of a waveguide is defined as $k_c=2\pi f_c\sqrt{\mu\epsilon}$. Then the complex-valued guided propagation constant is expressed as follows:

$$\gamma = jk\sqrt{1-\left(\frac{f_c}{f}\right)^2} \tag{1}$$

Therefore two guided propagation constants exist: (1) purely real, when the mode operation frequency is below the mode cutoff frequency $f<f_c$, the EM wave in this mode is attenuated $e^{-\gamma z}=e^{-\alpha z}$ and is called evanescent; (2) imaginary, when the mode operation frequency is above the cutoff frequency, the EM wave is not attenuated and is propagating, $e^{-\gamma z}=e^{-j\beta z}$. So the EM-wave in a certain mode is propagating only when the operation frequency is above the cutoff frequency for this mode. The cutoff frequency of a wave mode determines other parameters of the waveguide.

The wave impedance relates the transversal components of electric and magnetic fields of the wave as it is given below:

$$Z = \frac{E_t}{H_t} \tag{2}$$

Therefore it can be found that the wave impedance in the TE and TM modes is:

$$Z_{TE} = \eta\frac{k}{\gamma} = \sqrt{\frac{\mu}{\epsilon}} \bigg/ \sqrt{1-\left(\frac{f_c}{f}\right)^2} \tag{3}$$

$$Z_{TM} = \eta\frac{\gamma}{k} = \sqrt{\frac{\mu}{\epsilon}} \sqrt{1-\left(\frac{f_c}{f}\right)^2} \tag{4}$$

where $\eta$ is impedance of the medium.

The guided wavelength is derived from $k_c^2=k^2-\beta^2$ and $\beta=2\pi/\lambda_g$ and reads as follows:

$$\lambda_g = \frac{1}{\sqrt{\mu\epsilon}\sqrt{f^2-f_c^2}} \tag{5}$$

The cutoff frequency of the wave mode determines the propagation constant, wave impedance and guided wavelength. The cutoff frequency itself is dependent on a waveguide cross-section. A cross-section specific solution can be found for the longitudinal field component in combination with a boundary conditions on the metal and dielectric interface, which must be satisfied. There is no tangential electric and no normal magnetic fields to the metal interface. The transversal fields and mode cutoff frequency is found based on a result for the longitudinal field component. Under the perfect dielectric container resonance, the main waveguide mode exploited is the TE mode.

The phase condition of this resonance is determined by the following equations:

$$\int_{-r2}^{r2}\beta(z)dz \cong \pi \tag{6}$$

$$\beta(z) = \sqrt{k_0^2\epsilon_{eff}(z)-\left(\frac{m\pi}{a(z)}\right)^2-\left(\frac{n\pi}{b(z)}\right)^2} \tag{7}$$

$$\epsilon_{eff}(z) = \int_0^{a(z)}\int_0^{b(z)}\epsilon(x,y)E^2(x,y)dxdy \text{ for a } TE\text{-mode}$$

$$\epsilon_{eff}(z) = \int_0^{a(z)}\int_0^{b(z)}\frac{1}{\epsilon(x,y)}E^2(x,y)dxdy \text{ for a } TM\text{-mode}$$

$$\int_{-r2}^{r2}\sqrt{k_0^2\int_0^{a(z)}\int_0^{b(z)}\epsilon(x,y)E^2(x,y)dxdy-\left(\frac{m\pi}{a(z)}\right)^2-\left(\frac{n\pi}{b(z)}\right)^2}dz \cong \pi \tag{8}$$

The amplitude condition can be determined once the phase values are converted to equivalent impedances, effective index or effective permittivity:

$$Z_{TE} = \eta\frac{k}{\gamma} = \sqrt{\frac{\mu}{\epsilon}} \bigg/ \sqrt{1-\left(\frac{f_c}{f}\right)^2} \tag{9}$$

$$Z_{TM} = \eta\frac{\gamma}{k} = \sqrt{\frac{\mu}{\epsilon}} \sqrt{1-\left(\frac{f_c}{f}\right)^2} \tag{10}$$

Figure 3:
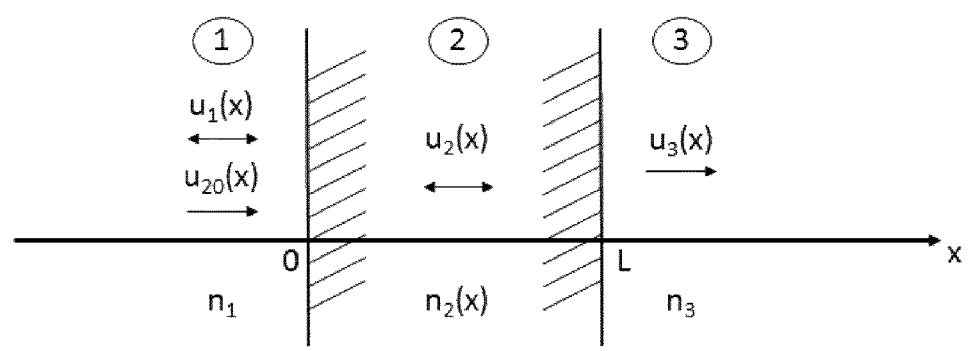
FIG. 3 shows the geometry of the electromagnetic problem of the discontinuity of the disclosed sensor.

Let the plane electromagnetic harmonic wave of the type $u_0(x)=A_0e^{-ik_1\cdot x}$ fall on a layer of thickness L having a refractive index $n_2(x)$ from a homogenous isotropic medium (see FIG. 3). It is necessary to find the diffracted field or, more precisely, the reflected and transited waves and a field in a layer $u_2(x)$. The function $u(x)$, which is continuous everywhere, as is derivative satisfies the operation:

$$u''(x)+k^2(x)u(x)=0, x \text{ being a real number} \tag{11}$$

Thus the diffraction problem is reduced to an ordinary differential operation:

$$u''_2(x)+k_2^2(x)u_2(x)=0, 0<x<L \tag{12}$$

with boundary conditions $u''_2(0)-ik_1u_2(0)=A_0$, $u'_2(L)+ik_3u_2(L)=0$, where $k_j=k_0n_j$ are wavenumbers of the media. $U(z)=E(z)$ of $H(z)$ for the TE and TM mode respectively.

The case is considered in which the refractive index (wavenumber) of a layer monotonically increases and then monotonically decreases. Cases of the linear, parabolic, sinusoidal, exponential and logarithmic refractive index profiles are investigated. The problem of the diffraction on a layer is solved for the linear problem analytically. For other problems a numerical analysis was performed. The method of approximating an integral identity is applied to increase accuracy of the grid solution to the obtained boundary problem.

Figure 4:
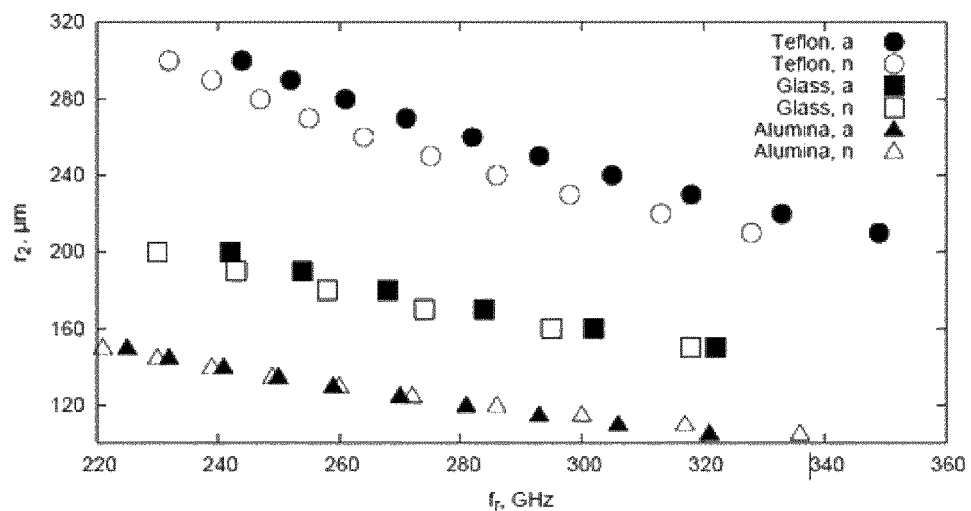
FIG. 4 shows the resonance frequency of the dielectric container without insertion opening as function a dimension of the sample holder obtained via analytically (a) and numerically (n) equation solving.

As discussed, a certain standing wave profile or a resonance mode is formed along the waveguide section loaded with a dielectric container. At the resonance frequency reflected EM waves along the dielectric container cause a constructive or destructive interference, whereby the phase difference ($\Delta\phi=\beta\cdot z$) is a multiple of $\pi$ or $\pi/2$, respectively. Increase of waveguide loading with a dielectric material (with higher dielectric permittivity) reduces the cutoff frequency, which in turns leads to an increase of phase constant, $\beta$, and reduces impedance, $Z_{TE}$. As can be seen form FIG. 4, increasing the outer radius of a dielectric container, r2, causes the resonance frequency to decrease, because i) the length of the dielectric container is increasing and ii) phase constant is increasing. FIG. 4 shows the resonance frequency of such loaded waveguide section without the insertion opening (2) for different materials of the dielectric container and as function of the outer diameter r2 of the dielectric container (4). The analytical (a) and numerical (n) solutions of the differential equations corresponds well.

A second resonance is this of the sensor without the sample or sample holder. The sensor only comprises the waveguide and the discontinuity, illustrated below as a longitudinal slot. By creating discontinuities, such as openings, on the rectangular waveguide, one introduces waveguide discontinuities, which gives rise to infinite number of TE and TM modes at the location of discontinuity. Depending on the dimension of the waveguide, the dielectric load inside the waveguide caused by the composite dielectric section and the changed boundary conditions, one can determine if the induced higher order modes are propagating or not. Nevertheless, the presence of the slot changes the impedance of the waveguide which is determined by the propagation constant of the electromagnetic wave. However, one can introduce again the concept of an effective waveguide where at each cross-section an effective dielectric index can be defined and hence a propagation wave vector and dielectric impedance. Typically the length OL of the slot (2) is larger than its width OW, for an efficient excitation of the so called pure sample holder/sample resonance in a closed waveguide system, i.e. resonance in a waveguide without slot opening as discussed below. Typically the width OW should be less than ¼ of the resonance wavelength.

The dimensions of the discontinuity impact the resonance frequency of the sensor without sample or sample holder.

Figure 5:
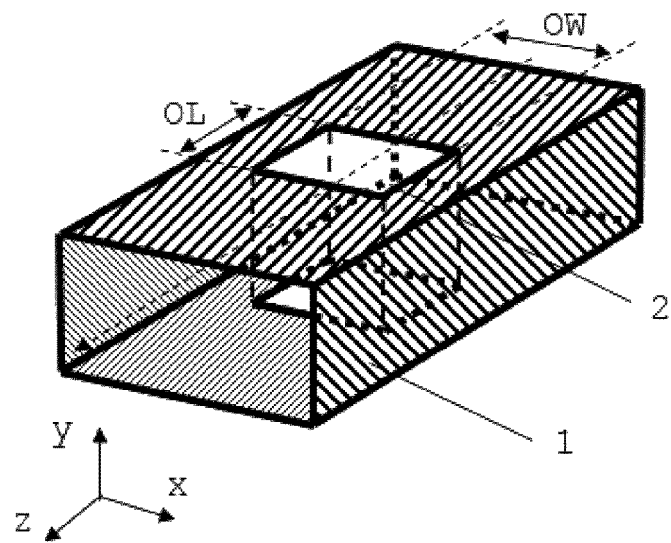
FIG. 5 shows the dimensions of the discontinuity causing the second resonance in the disclosed sensor.
Figure 6:
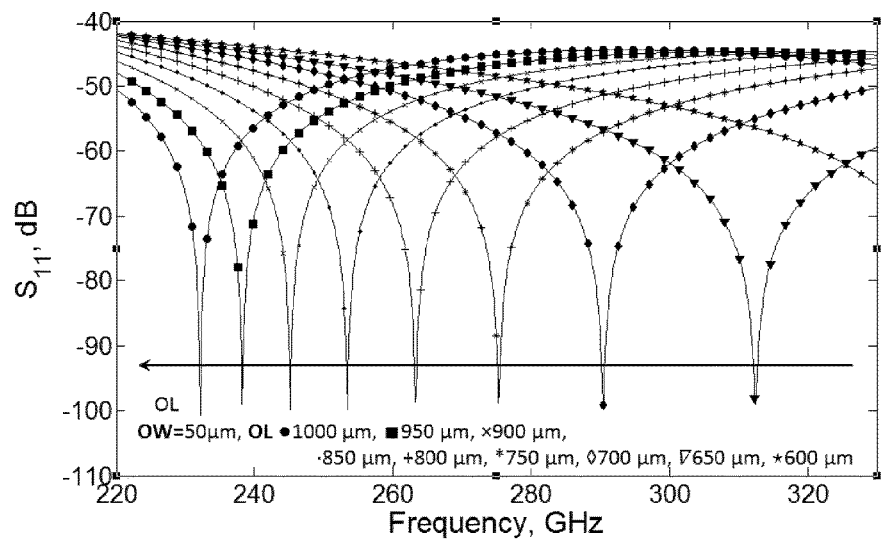
FIG. 6 shows the resonance in a disclosed sensor as function of the slot length OL.

In FIG. 6, the length OL of the slot (2) is swept from 600 um to 1000 um in steps of 50 um while the width OW is fixed at 50 um (micrometer). For small width OW, the resonance frequency is inversely proportional to length OL. The arrow indicates the increase of the OL, i.e. the resonance curve with the largest value for OL (1000 um) is on the left side. A waveguide with a discontinuity as shown in FIG. 5 forms a resonator which can be represented by three uniform waveguide sections connected in series with the corresponding impedances: $Z_{WG}$, $Z_{IO}$ and $Z_{WG}$. Where $Z_{WG}$ is an impedance of a waveguide section before and after insertion opening and $Z_{IO}$—impedance of a waveguide with an insertion opening. At constant OW, the impedance $Z_{IO}$ is not changing. The length OL determines the electrical length of the waveguide section with the insertion opening, which forms a resonator. Therefore the resonance frequency is inversely proportional to the length of the resonator section ($\beta\cdot l(OL)=\pi$), which is seen from FIG. 5.

Figure 7:
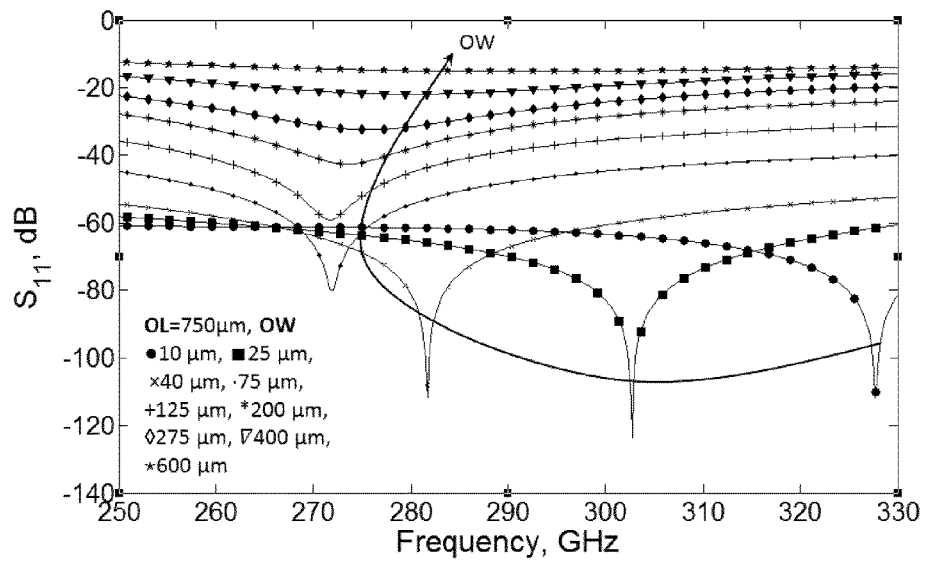
FIG. 7 shows the resonance in a disclosed sensor as function of the slot width OW.

In FIG. 7, the width OW of the slot (2) is varied 10, 20, 25, 30, 40, 50, 75, 100, 125, 150, 175, up to 600 um while the length OL is fixed at 750 um. For a fixed length, the resonance frequency is inversely proportional to the width up to a certain value W. For larger values of W, the resonance frequency does not shift anymore, but the amplitude of the resonance weakens more and more. The arrow indicates the increase of the OW, i.e. the resonance curve with the largest value (175 um) for OW is on the left side. The width of the insertion opening, OW, affects the EM field distribution of the propagating mode. First, OW affects the cutoff frequency of the propagating mode. As it can be seen from FIG. 6, the resonance frequency is decreasing with increasing OW ($\beta(OW\uparrow, f_r\downarrow)\cdot l=\pi$), which indicates that propagation constant $\beta$ is increasing with the increase of OW. Second, the impedance of the waveguide section with insertion opening, $Z_{IO}$, is changing with OW, as the impedance mismatch causes higher reflection with larger OW. Third, insertion opening radiates EM wave into free-space, causing leakage. The loss is directly related to OW, because the resonance Q-factor is decreasing with OW. This way the design of insertion opening enables to tune phase constant, $\beta$, impedance, Z, and losses, $\alpha$, of the waveguide section.

Figure 8:
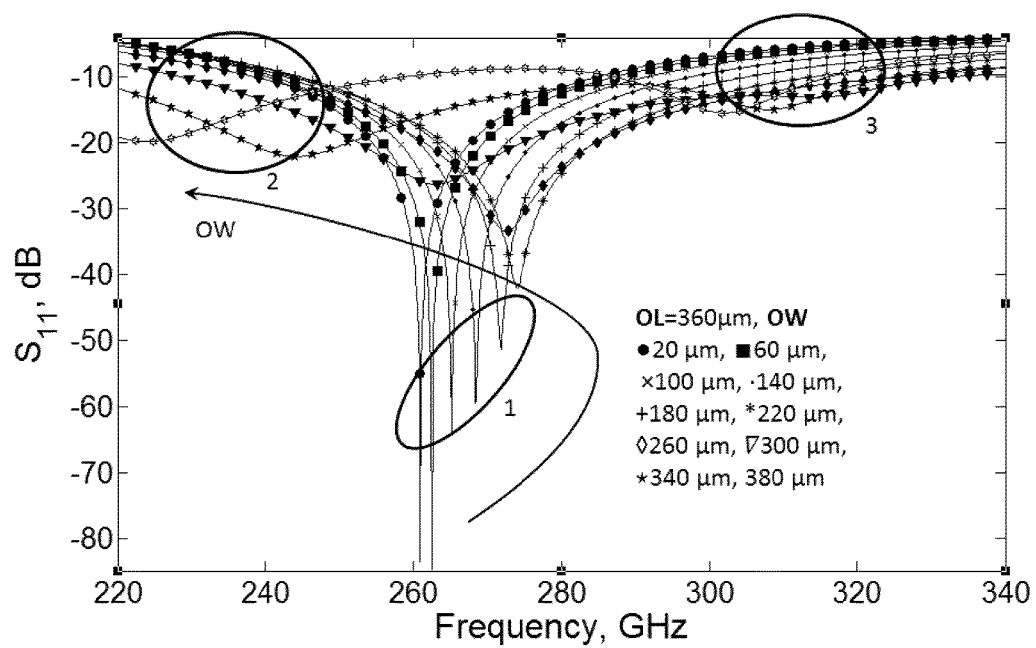
FIG. 8 shows the resonance behavior of a complete disclosed sensor showing the 3 resonance frequencies (1, 2, 3).

The complete sensor comprising the discontinuity and the sample holder hold one or two resonances depending on the combination of parameters. For narrow slot widths, OW only one resonance emerges, the so-called pure sample holder/sample resonance, whose frequency increases with the OW value (1) up to a certain range of OW values (<25% of free space resonance wavelength); for larger values of OW up to about the sample holder width, a second resonance type (2) emerges, expressing a mixed slot width—sample holder/sample resonance, finally for larger OW values a third resonance (3) emerges at higher frequencies, expressing a hybrid mode slot width resonance as illustrated in FIG. 8, with OL=360 um, OW is swept from 20 to 400 um with a step of 20 um.

Figure 9A:
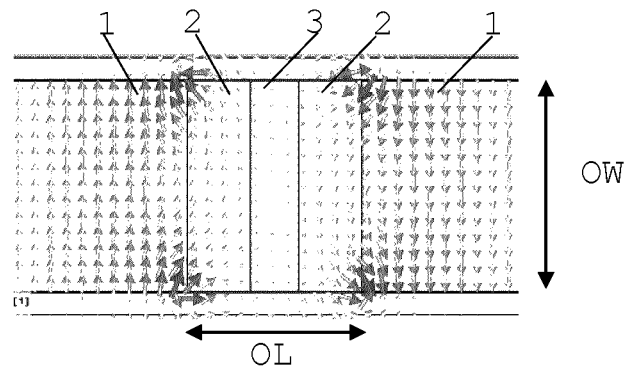
FIGS. 9a to 9c show the electrical field distribution for the different resonance modes as determined by the dimensions of the opening: a) $1^{st}$ resonance, OL=360 um, OW=360 um, f_resonance=233.68 GHz, b) $2^{nd}$ resonance, OL=360 um, OW=360, f_resonance=304.72 GHz, c) OL=460 um, OW=460 um, f_resonance=291.76 GHz.
Figure 9B:
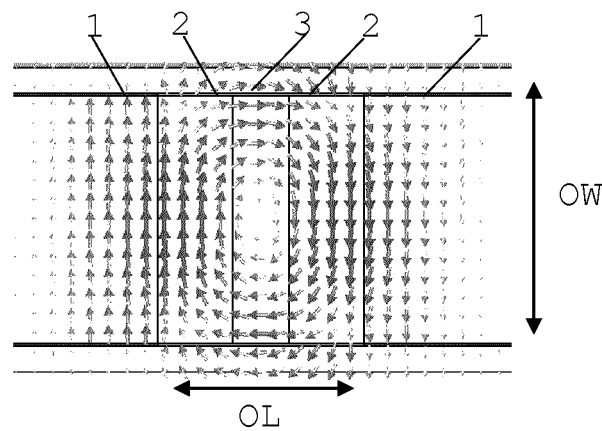
Figure 9C:
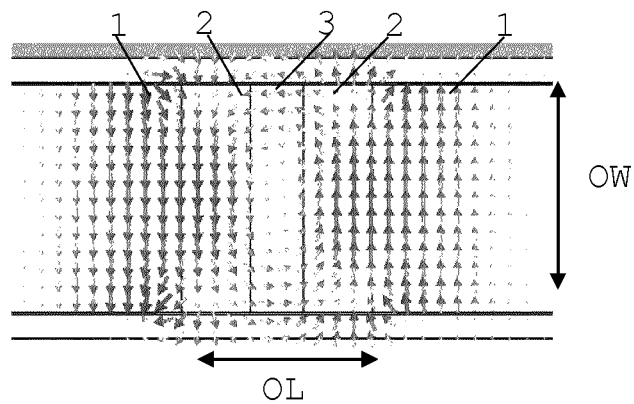

FIGS. 9a to 9c shows the electrical field distribution on a vertical plane along the propagation direction in the waveguide (1). FIG. 9a shows this field distribution for a mixed 'slot (2) width—sample holder (4)/sample (3)' resonance. Longitudinal E-fields are created due to fringing effect of the insertion opening (2) with negligible leakage through the opening (2) as indicated by the few horizontal E-field lines. FIG. 9b shows this field distribution for a 1 hybrid mode slot width ' resonance. Here the electric field leakage through the insertion opening is increased. In FIGS. 9a and 9b, the electrical field distributions of two resonance modes are shown: a) mixed slot width-sample holder/sample resonance and b) hybrid mode slot width resonance. By optimizing the dimensions (OL, OW) of the insertion opening (2), a combination of these two resonances is achieved as shown in FIG. 9c. Here an optimized complex impedance profile (amplitude and phase conditions) is achieved yielding the highest resonance Q-factor.

Figure 10:
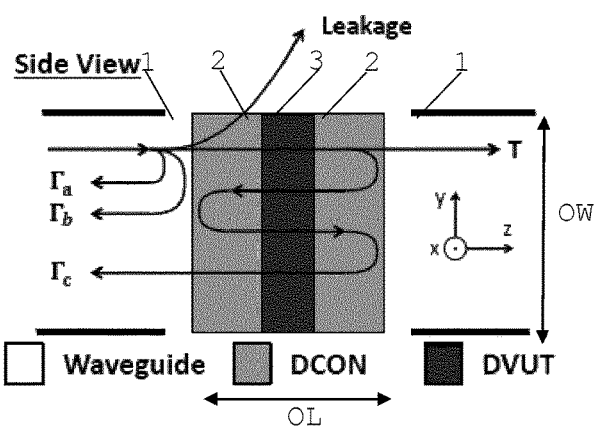
FIG. 10 illustrates the principle of the loaded composite dielectric section.

The additional reflection, caused by the introduced insertion opening edge, enables to achieve a stronger destructive interference in the reflection. Therefore the total reflection is greatly minimized (i.e. $S_{11}$<−70 dB) at the resonance frequency when all the backward propagating EM waves reflected on different features of the structure superimpose with maximally equal amplitude distributions with opposite phases. Consider FIG. 10 where the launched EM wave is reflected at: a) insertion opening (2) with a phase $\angle \Gamma_a = 0°$; b) the 1st boundary of sample holder (4)/sample (3) with phase $\angle \Gamma_b = 180°$; c) sum of backward transmitted EM waves from the multiple reflection within sample holder/sample, phase $\angle \Gamma_c = 0°$. The sum of these reflections is written as follows:

$$\Gamma_\Sigma = |\Gamma_a|e^{j0} + |\Gamma_b|e^{j\pi} + |\Gamma_c|e^{j0} \quad (13)$$

Figure 11:
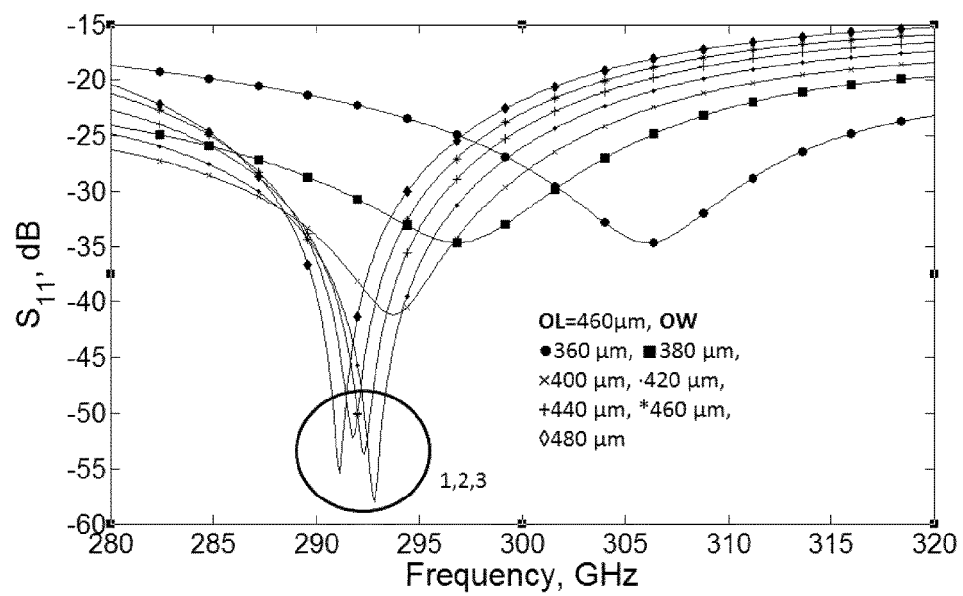
FIG. 11 shows the resonance behavior of a complete disclosed sensor whereby the resonance frequency of the three resonance mechanisms (1, 2, 3) coincides.

For another combination of these parameters, one can make the three resonances collaborate, as illustrated in FIG. 11.

Figure 12:
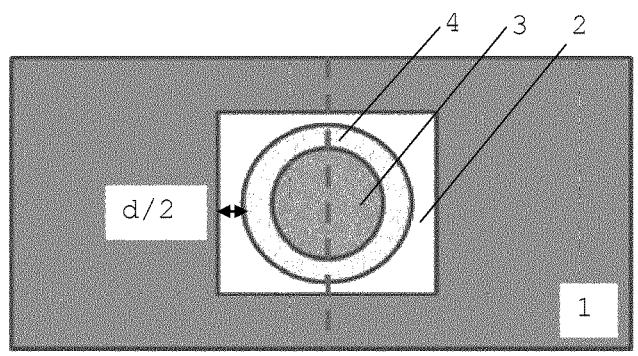
FIG. 12 shows a top view of a disclosed waveguide, the grey area is the unperturbed waveguide (1) having an impedance Z0.

In FIG. 12, the section of the waveguide (1) (grey) where the sample (3) is contained in a sample holder (4). The sample holder is spaced apart from the waveguide by an opening (2) creating a discontinuity in the propagation path of the electromagnetic waves. The electromagnetic sensing wave is propagating from left to right; this is called the z-direction. In the opening one can observe the hollow capillary tube (4) or hollow dielectric container, which is filled with the sample (3) under test. The middle of the container is indicated with a symmetry line.

Figure 14:
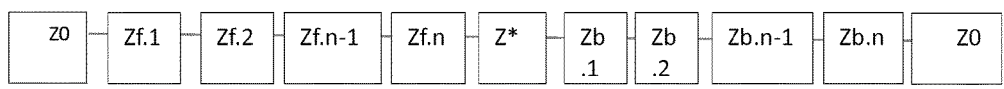
FIG. 14 shows an equivalent of a disclosed waveguide (impedance Z0) and the composite dielectric section divided in a section at the front side (comprising n discrete sections, each having an impedance Zf.i) and at the backside (comprising n discrete sections, each having an impedance Zb.i) w.r.t. the center of the composite dielectric section, having an effective impedance Z*.

According to the theory discussed above, one can again say that for each coordinate z, one can define a local impedance Zf.k or Zb.k where Zf.k and Zb.k are visualized in FIG. 14. Also an equivalent permittivity or refractive index can be defined based on the local materials. Hence the figure below demonstrates for three cross-sections how the local propagation characteristics and impedance can be calculated as was done for the previous resonance mechanisms.

Sensor Operation

A sensor configuration is developed comprising a sample integrated inside an electromagnetic waveguide. Preferably a hollow low-loss air-filled or low index and low loss material filled metallic waveguide is used. The sensor configuration comprises the coupling of an electromagnetic wave provided by a transmitter into the hollow metallic waveguide featuring a impedance $Z_0(f)$ which is dependent on the frequency f. Then the electromagnetic signal propagates to the sample, afterwards the electromagnetic signal needs to be coupled further on to the receiver side. This implementation concentrates the energy of the electromagnetic wave in the sample. The sample is hence placed substantially at the position of maximum electromagnetic energy.

In order to bring the electromagnetic signal with minimal signal loss from the unperturbed transmission line having impedance Zo towards the symmetry line of the sample (see vertical dashed line in FIG. 12), which is defined as the line where one has the largest cross-section of the dielectric disturbance, one needs an anti-reflective element on either side of symmetry line acting together as a half wavelength resonator at the resonance frequency.

This can be done with a coating of a single ARC layer (anti-reflective coating). However for any given transition from a material A with refractive index nA to a material B with refractive index nB, only one material exists which can provide a real zero reflection coefficient a this transition, namely the material which refractive index equals the SQRT (nA·nB) whereby its thickness is set equal to (2m+1) times $\lambda/4$ (m=0.1 . . . ). If such material physically does not exist, one can try implementing the half wave length resonator with a multi-layer coating system having consecutively a higher and lower refractive index values than the ideal single layer material mentioned before.

Another form of such a multi-layer system is a graded refractive index multi-layer system. Normally, this gradient is obtained by continuously changing the composition and configuration of the waveguide, in the direction of propagation of the wave, resulting in the optimized profile of the refractive index or impedance profile. In this disclosure, this gradient refractive index/impedance profile is implemented by changing along the propagation direction the transverse profile of the composite dielectric section comprising the sample, optionally contained in a sample holder, and a discontinuity. In theory an optimized impedance profile exists for given boundary conditions when going from impedance Zo at the input of the waveguide towards impedance Z* of the composite dielectric section and the again to Zo at the output of the waveguide. When one realizes this tapered transition, the reflection coefficient is minimum at the resonance frequency leading to a maximized quality factor, taking into account all possible losses in the tapered region. The resonance frequency of the waveguide is be largely determined by the size of the sample holder (see section above on resonance mechanisms), when the external radius $r_2$ is about the double of the internal radius $r_1$.

Figure 15:
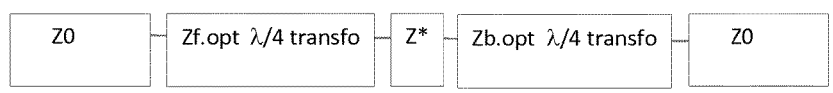
FIG. 15 shows an equivalent schema illustrating the half wave length resonator operation, as a combination of two quarter wave impedance transformers, of a disclosed sensor.

In other words, the opening (2) as illustrated in FIG. 12 in combination with the sample (3), optionally contained in a sample holder (4), can be viewed as two optimal $\lambda/4$ transformers in series with ideal cross-sectional shapes and material combinations, as illustrated by FIG. 15. These transversally shaped $\lambda/4$ transformers have the additional benefit that they also acts as a focusing element. They confine the EM energy once more towards the center of the waveguide. This has the advantage that it is a second way of energy compression thereby maximizing the interaction between the wave with the sample.

Hence the sensor proposed here combines a gradient or tapered impedance/index profile along the propagation direction by a transverse material distribution which additionally acts like an energy focusing element. In order to avoid any return of the signal after its interaction with the sample, an ARC element as described above is provided. In this case, essentially no absorption occurred in the sample (3), a fully symmetric structure can be proposed such that the sections before the sample and after the sample, along the propagation direction, are fully symmetric with respect to the center of the sample plane. This is then called the backside $\lambda/4$ transformer with impedance Zb.opt.

An example of such a tapered implementation is e.g. inserting a sample holder in the form of a cylindrical capillary tube, with a circular cross-section, orthogonally to the propagation direction of the EM wave. In practice a capillary tube has a circular shape, which intrinsically induces a quasi-adiabatic transition i.e. without reflection losses. Inside the cylindrical dielectric container, i.e. the hollow capillary tube, one delivers the sample under test. Hence for any given combination of capillary tube (CT) and sample material, one obtains an equivalent impedance at the symmetry plane of the filled cylinder (see FIG. 9).

Propagating from the air-filled hollow waveguide towards the symmetry plane of the sample, one meets cross-sectional planes with increasing width of capillary tube material, then once at the internal edge of the capillary tub, one meet the maximum cross-section comprising waveguide, opening filled with air surrounding the capillary tube, the wall of the sample holder and the maximum cross section of the sample. By default, this circular profile, which behaves like a continuous quasi-adiabatic profile, leads to a small reflection coefficient at the resonance frequency. If this combination of opening, sample holder and sample does not deliver an optimum index profile such that a minimized reflection coefficient is obtained at the resonance frequency, means are provided to the sensor to tune the sensor towards the phase and amplitude matched conditions such that an optimized combination of two λ/4 transformers is obtained.

Electromagnetic Impedance Tuner

A sensor for dielectric spectroscopy of a sample is disclosed, the sensor comprising a waveguide inductively loaded with a composite dielectric section which comprises a sample holder and a discontinuity separating the sample holder from the waveguide, whereby the electromagnetic impedance of the composite dielectric section varies gradually, at least along the propagation direction of the waveguide, at least from the onset of the discontinuity towards the sample holder, whereby the composite dielectric section further comprises a electromagnetic impedance tuner.

In most practical cases, a physical opening (discontinuity) is provided for the injection of a capillary tube (sample holder (4)) into the waveguide (1). The extra space between the waveguide edge and the capillary tube edge itself, is called the clearance (CL). The waveguide section corresponding to the clearance can also be considered as a part of a transmission line with a complex valued impedance due to the narrow slotted opening of the clearance. Hence this section acts as an additional transmission line element providing amplitude and phase matching properties to reach an optimized λ/4 transformer at each side of the sample. Hence the capillary tube and the additional clearance lead to the desired transformer.

It has been explained in the previous paragraphs that, for a given sample material (3) inside the sample holder (4), the composite dielectric section structure can be optimized at the resonance frequency. The structure is extremely sensitive for dielectric permittivity changes. However when the sample material is changing, e.g. due to buffer change in a liquid or other liquid mixture composition, the sensor loses its high-performance resonance. Hence means are provided to bring the sensor back in resonance with minimized reflection which is determined by the losses in the unperturbed waveguide and in the sample holder for a given sample in the sample holder. This tuning can be done by local beta or impedance changes. Various implementations of such tuning exist: tuning the dimensions of the opening, dual liquid sample holder containing the sample and a second variable liquid, tuning the dimensions of the sample holder or tuning the cross-section of the composite dielectric section.

Hence to cope with various materials inside the sample holder, embodiments are disclosed to create an optimal AR-coupling between the waveguide and the sample.

Figure 13:
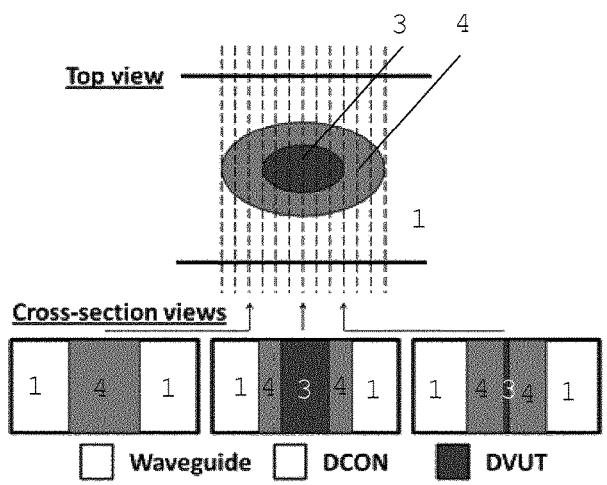
FIG. 13 shows a discretization of a disclosed waveguide (1) and the composite dielectric section (DCON=sample holder (4), light grey, DVUT=sample (3), dark grey).
Figure 16A:
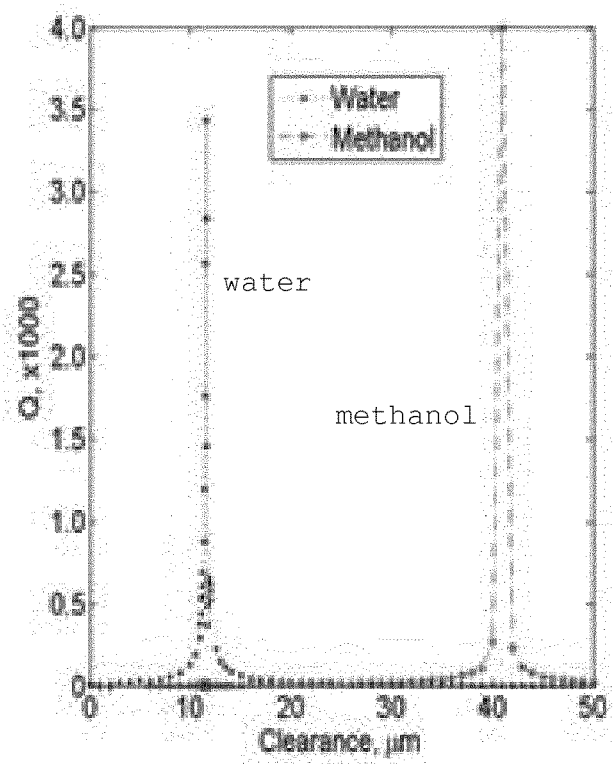
FIGS. 16a-16c show the disclosed sensor structure clearance (CL) parametric study: (a) Q-factor, (b) minimum reflection and (c) resonance frequency dependence on CL for a structure filled with water and methanol.
Figure 16B:
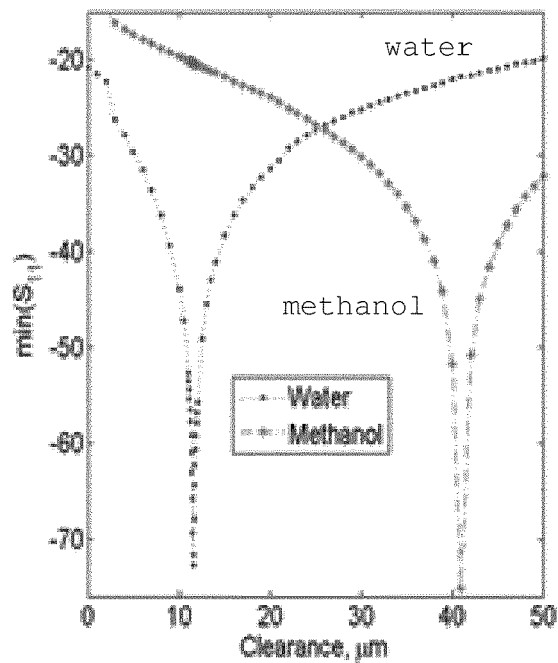
Figure 16C:
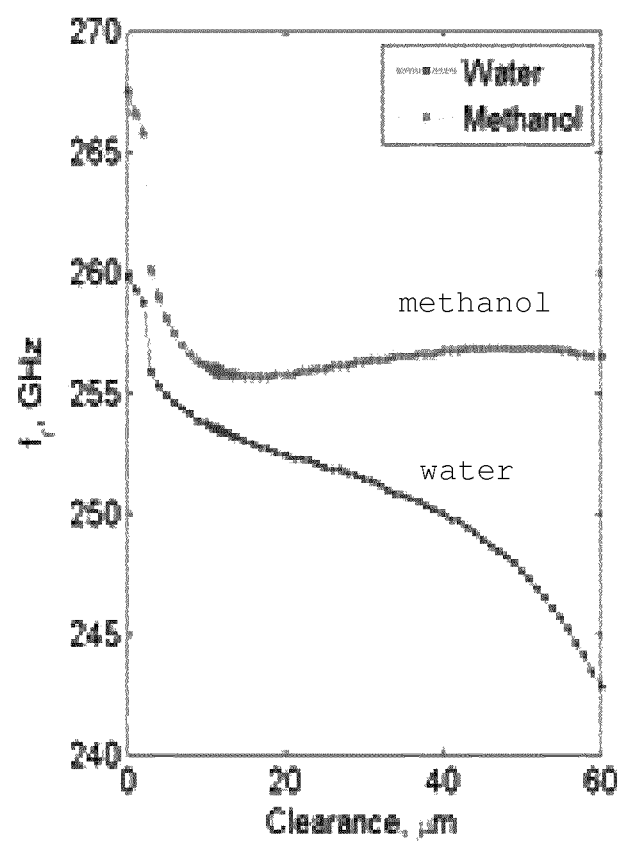

Varying the Dimensions of the Discontinuity p One of the preferred options is to create a variable clearance opening in front and or back of the capillary tube. Noticeably, the resonance in the reflection of the structure shown in FIG. 11 strongly depends on the size of the insertion hole size relative to the dimensions of the sample holder as shown in FIG. 13. The clearance opening is defined as half the size by which the insertion hole is larger than the outer diameter of the sample holder: clearance d=(opening.side−d2)/2) as shown in FIG. 12. Here the sample and sample holder are positioned in the center of the insertion hole. A clearance size in the structure shown in FIG. 12 can be chosen to increase the resonance Q-factor for a specific sample material. The structure with a rectangular hole with CL=11.6 μm exhibits sharp resonance with Q=3400 for water as sample, while the Q=4000 is achieved when CL=41 μm when the sample is methanol (see FIG. 16(a)). Introduction of insertion openings improves the resonance Q-factors by a factor of 100 and 10 for water and methanol, respectively. Small changes in the dimensions of the clearance results in significant resonance Q-factor changes: for water ΔCL=0.1 μm change gives ΔQ=600; for methanol ΔCL=1 μm results ΔQ=3700. Clearance size has often also a limited effect on the resonance frequency (see FIG. 16(c) for the case of methanol).

Figure 17A:
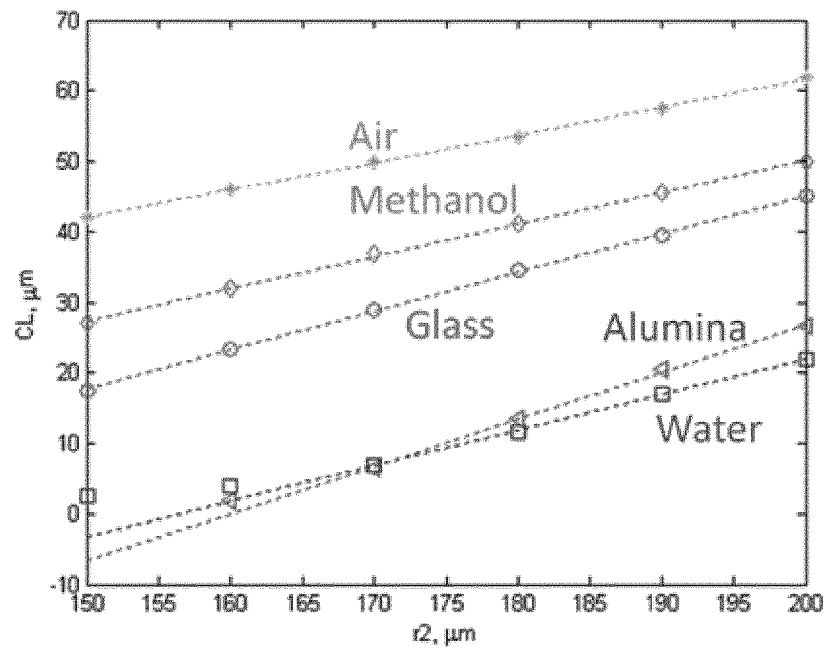
FIGS. 17a-17b show the optimized insertion hole clearance (CL) depending on the CT outer radius ($r_2$).
Figure 17B:
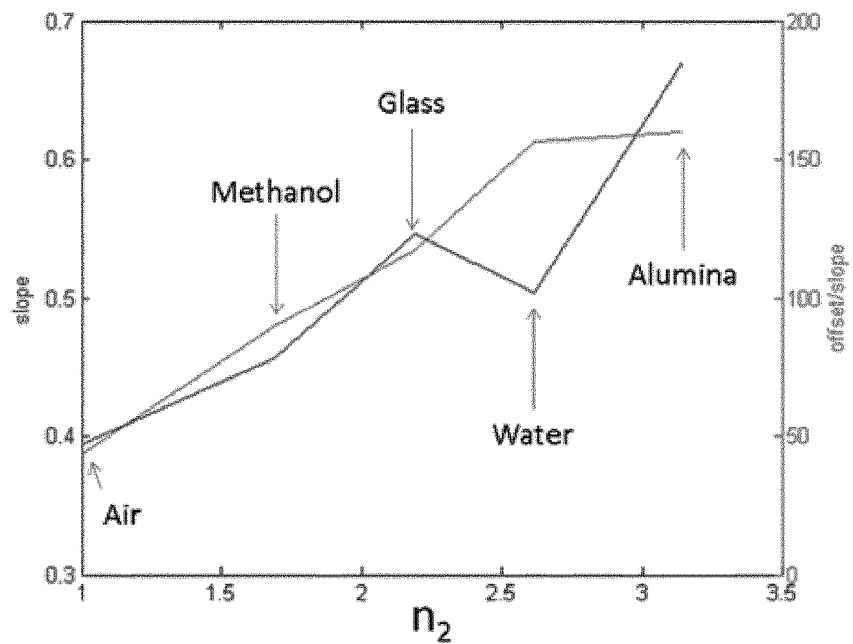

The clearance of the structure shown in FIG. 12 is optimized for a range of different sample materials and different outer radiuses, r2, of the sample holder (see FIG. 17(a)). For different sample materials, the clearance shows a linear dependency on the outer radius, r2, of the sample holder. The line (f(x)=slope·(x−offset/slope)) parameters are fitted and plotted versus the sample refractive index (see FIG. 17(b)). The outer radius of the sample holder determines the multilayered dielectric post resonance frequency. From FIG. 17(a), it is clear that with decreasing resonance frequency, hence with increasing resonance wave length, the dimensions of the clearance increases proportionally with a fraction of the resonance wavelength. The slope of the linear CL dependency on r2 is nearly the same for all the materials (see FIG. 17(b)). The linear dependency offset is dependent on the refractive index, n1, of the sample material. The offset is proportional to n1, so that the clearance is bigger for lower n1 (see FIG. 17(b)). Therefore optimal clearance can be found for different dielectric permittivity of the sample to achieve the highest sensitivity.

The whole structure parameter analysis reveals tight design tolerances. Very small design parameter deviations (<1%) lead to significant changes in the resonance Q-factor (>50%). Such a design tolerances can only be met with highly characterized micromachining technology. The dimension tolerances on the sample holder are much tighter than of the commercially available ones. Nevertheless, the free-standing capillary tube in the insertion opening makes it possible to fine-tune the structure response after the device manufacture. Therefore the tight dimensional tolerances are circumvented by fine tuning the capillary tube position in the insertion opening.

This variable clearance length allows tuning of both phase and amplitude, due to the small radiation losses. This tuning is expressed through the coupling coefficient between waveguide and the sample holder. The clearance opening introduces phase shift compensation: the larger the refractive index of the sample, the larger the optimal equivalent refractive index of the equivalent composite dielectric section needed for optimal coupling, hence less clearance needed. The clearance scales linearly with the radius of the sample holder: the larger the radius, the more clearance is needed to obtain the same effective index for the composite dielectric section. When the sample holder is filled with air, a smaller optimal equivalent refractive index of the composite dielectric section is needed; hence a larger clearance opening is needed.

The opening of the clearance is depending on all materials (sample/material under test (3) (LUT), the material of the capillary tube (CT) wall (4) and its geometrical parameters: r1, r2, the waveguide (1) cross-sectional dimensions). If r1 is substantially smaller than r2, the resonance frequency is hardly dependent on the material under test inside the capillary tube. The effective local effective wavelength can be determined at this resonance frequency. The clearance opening d is approximately related to the radius r1 multiplied by the effective wavelength inside the clearance section. This effective wavelength can be determined by solving the electromagnetic problem of a slotted waveguide section filled with air and then multiplied by the difference between the inverse of the effective wavelength at the symmetry plane, once filled with the material under test and once filled with a material leading to a zero clearance opening:

$$d_{CL}^{LUT} \cong r_1 \lambda_g^{CL} \left( \frac{1}{\lambda_g^*(r2, mat \cdot CT, r1, mat \cdot LUT)} - \frac{1}{\lambda_g^*(r2, mat \cdot cT, r1, mat \cdot ref0)} \right) \quad (14)$$

$$\lambda_g = \frac{1}{\sqrt{\mu\epsilon}\sqrt{f^2 - f_c^2}} \quad (15)$$

The clearance is only one of the options that can be proposed to design the ultimate $\lambda/4$ AR transformer.

Varying the Layout of the Discontinuity

Alternatively or additionally for obtaining minimum reflection coefficients, one can also shape the clearance opening or modify the shape of this clearance opening.

Figure 18:
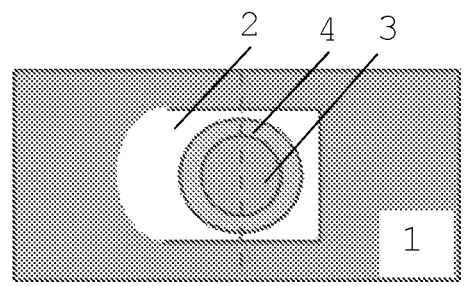
FIG. 18 illustrates shaping the clearance opening (white) of a disclosed sensor.

As the resonator structure is determined by minimization of the reflection coefficient, it makes sense to maximize the adiabatic characteristics of transitions in the structure. This is already obtained by the circular geometry of the capillary tube. The same can be applied to the clearance opening. This leads again to an improved figure of merit. As shown in FIG. 18, the clearance opening (2) (white area) has a graded curved section which introduces the gradual change of the electromagnetic properties from the waveguide edge (1) (grey) towards the edge of the sample holder (4).

Figure 19:
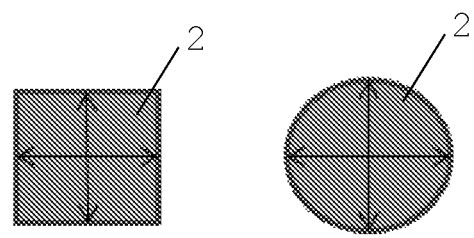
FIG. 19 illustrates different layouts of the clearance opening of a disclosed sensor, from left to right: square opening, circular opening.
Figure 20:
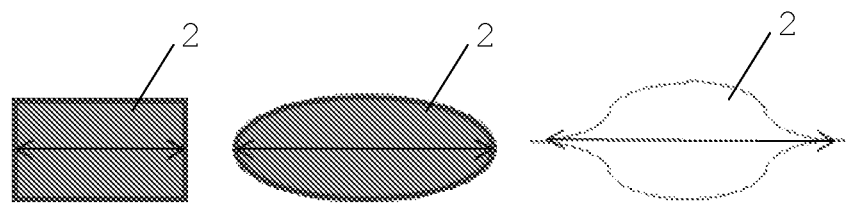
FIG. 20 illustrates different layouts of the clearance opening of a disclosed sensor, from left to right: rectangular opening, elliptical opening, eye opening.

Dimensioning of the waveguide opening is critical in the design of the sensor. Typically, prominent influence of the performance is expected with fabrication tolerance on the order of micrometers. That is the reason why the waveguide structure needs to be accurately fabricated. However, different geometrical topologies present different levels of sensitivity towards the fabrication tolerance. Two scenarios are explored for different shapes: (1) the dimension of the opening is changed both in x and z directions (see FIG. 19), (2) the dimension of the opening is changed along the propagation direction z (see FIG. 20).

From simulation it is found that the circular opening has sensitivity of about 14 db/um variation, while the square opening has a higher sensitivity of about 20 db/um.

From simulation it is found that for the same response (about 55 dB) the rectangular opening has a sensitivity of 4 dB/um, while the elliptical opening has a sensitivity of 2.15 dB/um. The "eye opening" is almost insensitive to variations in dimensions, 0.5 dB/um only, making it less favorable for tuning.

Figure 21:
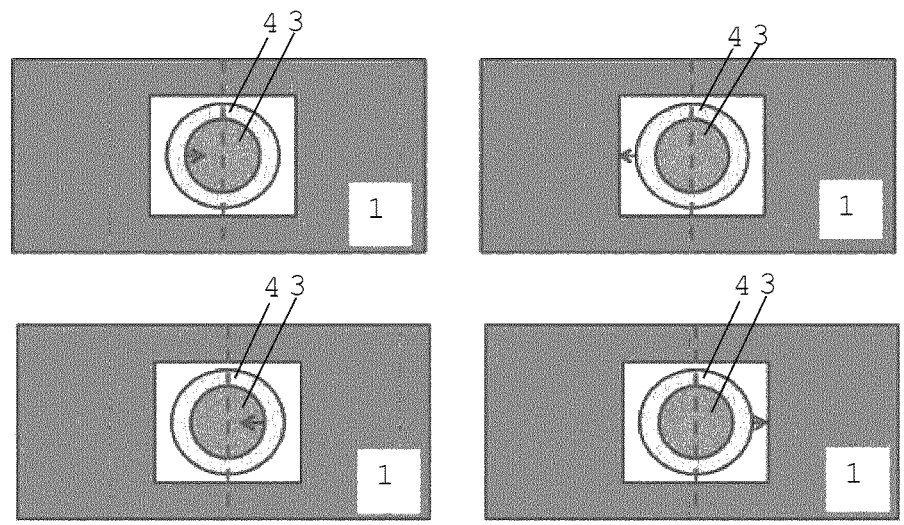
FIG. 21 illustrates shaping the clearance opening of a disclosed sensor by varying the inner ($r_1$) or outer ($r_2$) radius at one side along the propagation direction.
Figure 22:
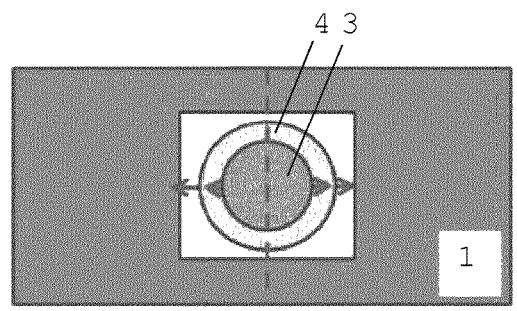
FIG. 22 illustrates shaping the clearance opening of a disclosed sensor by tuning the inner ($r_1$) or outer ($r_2$) radius of the sample holder.

Alternatively or additionally for obtaining minimum reflection coefficients, one can also shape or modify the shape of the sample holder. Various embodiments exist: adapting the internal radius of the wall of the sample holder as indicated by the arrow (front side and or backside: FIG. 21 left), adapting the external radius of the wall of the sample holder (front side and or backside: FIG. 21 right), adapting both the internal and external radius of the sample holder (front side and or backside: FIG. 22).

Providing a Sample Holder with a Differential Liquid System

Figure 23:
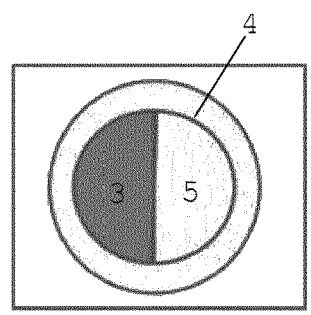
FIG. 23 shows a dual chamber sample holder of a disclosed sensor comprising a material in addition to the sample.
Figure 24:
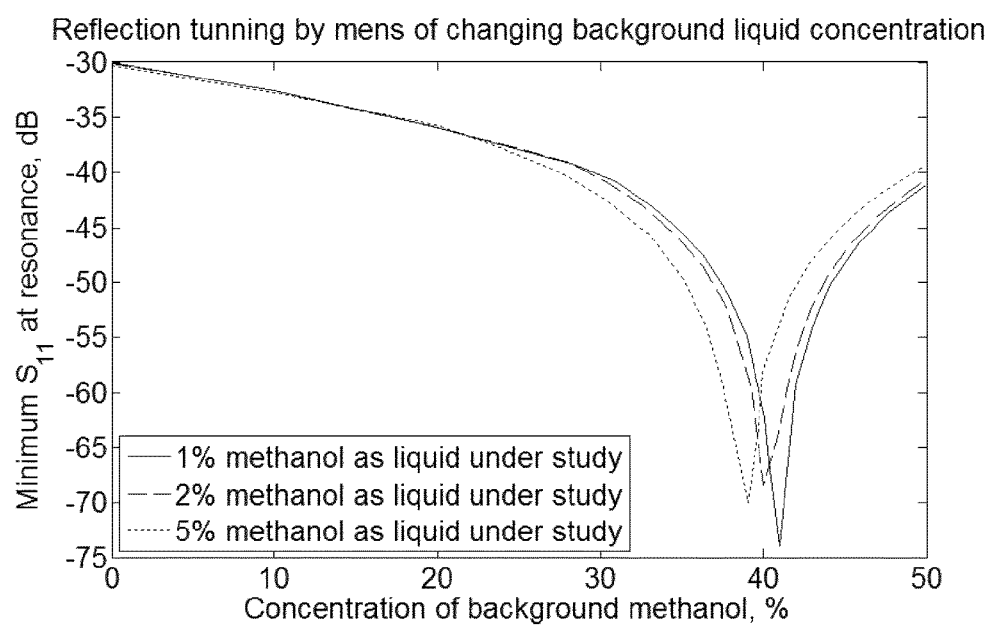
FIG. 24 shows the dependency of the reflected signal of a disclosed sensor on the composition of the material.

In FIG. 23, one observes that for a given non-optimal clearance opening, the content of the second chamber (5) in the sample holder can be changed to obtain minimum reflection coefficient. A chamber of the sample holder is filled with the sample (3) (1, 2 or 5% methanol); the second chamber (5) is filled with a matching liquid. One observes in FIG. 24 that: for 1% methanol water-methanol mixture, the optimal methanol content in the second chamber=41% methanol; for 2% methanol water-methanol mixture, the optimal methanol content in the second chamber=40% methanol; for 5% methanol water-methanol mixture, the optimal methanol content in the second chamber=39% methanol.

Deforming the Cross Section of the Composite Dielectric Section

The deformation of the section around the slot opening will induce a local impedance change such that again the optimal impedance tapering can be obtained.

Measurement

A method for operating a sensor according to any of the foregoing paragraphs is disclosed, the method comprising: introducing a sample in the sample holder, and measuring the response of the waveguide. Before introducing the sample, one can calibrate the sensor by introducing a reference sample in the sample holder and tuning the sensor thereby minimizing the reflection signal at the resonance frequency. In addition or alternatively one can, before calibrating the sensor with the reference sample, further calibrating the electromagnetic impedance tuner by introducing a calibration element into the sensor and tuning the sensor thereby minimizing the reflection signal at the resonance frequency.

Static Versus Dynamic

A static approach can be applied. For each reference material, an optimum position is selected such that the absolute minimum signal reflection is reached. Then the sample (3) is injected, e.g. concentration C1 of biomolecule B1, and the change in response with respect to the reference material is recorded.

A dynamic approach can be applied. For each material introduced into the system, a periodic tuning of one of the tunable parameters is performed. This periodic tuning avoids the time consuming job of the static approach. The tuning range is selected in accordance with the maximum and minimum dielectric permittivity of the materials. The tuning step is small enough to determine the absolute minimum reflection. The tuning parameter is periodically swept with the sweeping step. For each tuning step the reflection coefficient is recorded through a data acquisition system, comprising an ADC. This periodic excitation/tuning introduced a much better signal-to-noise ratio compared to lock-in detection algorithm.

Methods

The concentration dependence for a known solvent mixture, e.g. buffered solution, with known solute but unknown concentration after calibration can be determined. The tuning of sensor can be optimized for sensitivity and dynamic range by tuning the sensor such that the reference solutions yields the resonance response, any detuning by concentration changes leading to an altered response.

Changes due to physic-chemical-bio changes inside the mixture can be observed. A mixture, e.g. solvent mixtures with solutes, is injected into the sample holder (4), and the time dependent response is observed. The data acquisition is in accordance with the expected speed of the bio-physico-chemical change: without external perturbation or with external perturbation such as e.g. PCR or Q-PCR, repetitive time dependent thermal cycling or ionic strength changes, pH changes.

Changes due bio-physico-chemical interactions inside the mixture can be observed as follows: (a) measurement of a solvent mixture with solute A in concentration CA, leading to response RA, (b) measurement of a solvent mixture with solute B in concentration CB, leading to response RB, (c) measurement of a solvent mixture with solutes A and B in concentration $C_A$ and $C_B$ and record the response RAB, (d) then calculate the differential response dR=RA+RB−RAB, and (e) if dR=0, no interaction takes place between molecules of type A and molecules of type B, if dR not 0, then a reaction between molecules of type A and type B is observed. This observation can be done without external perturbation or with external perturbation, e.g. PCR or Q-PCR, repetitive time dependent cycling.

The sensor configuration can be tuned towards the most sensitive output, as follows: (a) tune for a reference liquid, (b) bring the sample into the sample holder and record the response of the sensor, and (c) calculate the response difference between (a) and (b).

The sensor configuration can be periodically tune around the estimated most sensitive setting point as follows: (a) add the reference liquid, (b) apply a periodic tuning to the sensor configuration between a minimum and maximum value of a tuning parameter and record the response of the sensor such that the sensor output features a minimum output, (c) add the sample and apply the periodic tuning cycle of procedure step (b) thereby recording the time dependent sensor output and (d) extract the difference between output (b) and (c). Periodic tuning has the advantage that it is less time consuming.

If the sample is a biomolecule, in principle it is intrinsically label-free and immobilization free, but immobilization of binding partner might be done to increase the sensitivity.

Design

A method for designing a sensor for dielectric spectroscopy of a sample is disclosed, the sensor comprising a waveguide (1) inductively loaded with a composite dielectric section which comprises a sample holder (4) and a discontinuity separating the sample holder (4) from the waveguide (1), whereby the electromagnetic impedance of the composite dielectric section varies gradually, at least along the propagation direction of the waveguide, at least from the onset of the discontinuity towards the sample holder, the method comprising: selecting a frequency band, dimensioning the waveguide in accordance with the selected frequency band, and dimensioning the composite dielectric section as a quasi-half-wave length resonator within the selected frequency band.

When designing a sensor as disclosed in the foregoing embodiments, preferably the following steps are taken.

First, the electromagnetic frequency band in which the sensor is to be operated is selected in view of the samples (2) to be tested. This frequency band determines the dimensions of the waveguide (1), as this waveguide must convey electromagnetic signals within this frequency band towards the sample holder (4). Also the shape of the cross-section of the waveguide perpendicular to the propagation direction is selected.

Then, the geometry of the composite dielectric section is selected. Preferably the composite dielectric section is aligned with the waveguide to reduce losses. The cross-sectional shape of composite dielectric section can have be the same as the cross-sectional shape of the waveguide, e.g. square or hexagonal, but other shapes are possible.

Then, the material properties of the sample (2) are to be taken into account when further dimensioning the composite dielectric section. If the aggregation phase of the sample material is solid, no sample holder (4) is needed as the material (2) can be directly positioned within the discontinuity. For other aggregation phases, e.g. liquids, powders, gas, jelly, a sample holder (4) is needed in order to hold the sample during the measurement. If the electromagnetic absorption by the sample in the selected spectral band is low, then the volume of the sample holder can be selected for optimal sensitivity without attenuating the electromagnetic signal. However, if the electromagnetic absorption by the sample in the selected spectral band is high, the sample volume might be limited to prevent substantial attenuation of the electromagnetic signal. In the latter case, the ratio of the inner dimension/outer dimensions of the sample holder may be selected for optimal sensitivity without substantial attenuation of the electromagnetic signal.

Based on the above considerations, a first order design of the waveguide is determined, assuming no discontinuity or opening is present.

If no sample holder is present, the dielectric constant of the sample is determined, if not yet known. A layout of the discontinuity is selected, e.g. circular or elliptical, and the composite dielectric section is divided in discrete sections. The phase change of the electromagnetic signal over these discrete sections is integrated (see FIG. 10). The reflection coefficient Γ1 according to formulas given below for discrete set of N+1 frequencies in the frequency domain ΔF of interest: N×δf=Δf.

The phase condition for the dielectric resonator can be approximately defined as:

$$\int_{-r2}^{r2} \beta(z)dz \cong \pi \quad (16)$$

$$\beta(z) = \sqrt{k_0^2 \varepsilon_{\it{eff}}(z) - \left(\frac{m\pi}{a(z)}\right)^2 - \left(\frac{n\pi}{b(z)}\right)^2} \quad (17)$$

$$\varepsilon_{\it{eff}}(z) = \int_0^{a(z)} \int_0^{b(z)} \varepsilon(x, y)E^2(x, y)dxdy \text{ for a } TE\text{-mode}$$

$$\varepsilon_{\it{eff}}(z) = \int_0^{a(z)} \int_0^{b(z)} \frac{1}{\varepsilon(x, y)} E^2(x, y)dxdy \text{ for a } TM\text{-mode}$$

$$\int_{-r2}^{r2} \sqrt{k_0^2 \int_0^{a(z)} \int_0^{b(z)} \varepsilon(x, y)E^2(x, y)dxdy - \left(\frac{m\pi}{a(z)}\right)^2 - \left(\frac{n\pi}{b(z)}\right)^2} dz \cong \quad (18)$$

The amplitude condition to obtain minimal reflection can then be determined. Once the phase data is converted to equivalent impedances, effective index or effective permittivity, one can calculate the reflection coefficient of consecutive discrete sections in the composite dielectric section.

$$\Gamma_i = \frac{\rho_i + \Gamma_{i+1} e^{-2jk_i d_i}}{1 + \rho_i \Gamma_{i+1} e^{-2jk_i d_i}} \quad (19)$$

$$k_i = \frac{2\pi}{\lambda} \tilde{n}_i \quad (20)$$

$$\rho_i = \frac{\tilde{n}_{i-1} - \tilde{n}_i}{\tilde{n}_{i-1} + \tilde{n}_i} \quad (21)$$

$$\Gamma_{M+1} = \rho_{M+1} \quad (22)$$

$$Z = Z_0 \sqrt{\frac{\mu_r}{\epsilon_r}} \quad (23)$$

For non-magnetic materials, the refractive index is inversely proportional to the material's characteristic impedance.

$$Z = \frac{Z_0}{n} \quad (24)$$

$$\partial \frac{\left\{ \frac{\partial \Gamma_1(\text{profile}(Zi))}{\partial f} \right\}}{(\text{profile}(Zi))} = 0 \quad (25)$$

$$Z_{TE} = \eta \frac{k}{\gamma} = \sqrt{\frac{\mu}{\epsilon}} / \sqrt{1 - \left(\frac{f_c}{f}\right)^2} \quad (26)$$

$$Z_{TE} = \eta \frac{k}{\gamma} = \sqrt{\frac{\mu}{\epsilon}} / \sqrt{1 - \left(\frac{f_c}{f}\right)^2} \quad (27)$$

$$Z_{TM} = \eta \frac{\gamma}{k} = \sqrt{\frac{\mu}{\epsilon}} \sqrt{1 - \left(\frac{f_c}{f}\right)^2} \quad (28)$$

When the resonance frequency thus obtained is not within the selected frequency band, the layout of the discontinuity is adjusted. The above determination is repeated until the resonance frequency thus obtained is within the selected frequency band.

If a sample holder is present, the dielectric constant of the sample and of the material of the sample holder is determined, if not yet known. A layout of the discontinuity and of the sample holder is selected. For the sample holder the inner and outer dimension of its wall is selected taking into account the absorption properties of the sample. As done above, the composite dielectric section is divided in discrete sections. The phase change of the electromagnetic signal over these discrete sections is integrated (see FIG. 10). The reflection coefficient Γ1 according to formulas given above for discrete set of N+1 frequencies in the frequency domain ΔF of interest, is N×δf=Δf. When the resonance frequency thus obtained is not within the selected frequency band, the layout of the discontinuity and/or the sample holder is adjusted. The above determination is repeated until the resonance frequency thus obtained is within the selected frequency band.

The invention claimed is:

1. A sensor for dielectric spectroscopy of a sample, the sensor comprising:
a waveguide including a composite dielectric section, wherein the composite dielectric section comprises a sample holder and a discontinuity separating the sample holder from the waveguide, wherein a first section of the waveguide at a first side of the composite dielectric section is symmetrical with a second section of the waveguide at an opposing second side of the composite dielectric section,
wherein an electromagnetic impedance of the composite dielectric section varies gradually, at least along a propagation direction of the waveguide, and at least from an onset of the discontinuity towards the sample holder,
wherein the composite dielectric section has a transverse profile in a cross-section of the composite dielectric section perpendicular to the propagation direction of the waveguide,
wherein a change in the transverse profile along the propagation direction of the waveguide causes the electromagnetic impedance to vary gradually with a tapered impedance profile, and
wherein the composite dielectric section is arranged in the waveguide such that the waveguide extends on opposite sides of the composite dielectric section along the propagation direction of the waveguide and that the waveguide at the first side of the composite dielectric section along the propagation direction of the waveguide has an electromagnetic impedance ($Z_0$) which is equal to an electromagnetic impedance ($Z_0$) of the waveguide at the second side of the composite dielectric section along the propagation direction of the waveguide.

2. The sensor of claim 1, wherein the composite dielectric section constitutes a dielectric resonator configured as a quasi-half wavelength resonator.

3. The sensor of claim 2, wherein the electromagnetic impedance of the composite dielectric section is configured to yield minimal reflection at a resonance frequency of the dielectric resonator.

4. The sensor of claim 1, wherein the discontinuity is an opening defined by the waveguide.

5. The sensor of claim 4, wherein the sample holder is a capillary tube disposed in the opening.

6. The sensor of claim 5, wherein the discontinuity includes a curved section and a straight section.

7. The sensor of claim 5, wherein the capillary tube extends at least from a first side to an opposite second side of the composite dielectric section in a direction perpendicular to the propagation direction of the waveguide.

8. The sensor of claim 5, wherein the discontinuity is a square opening.

9. The sensor of claim 1, wherein the composite dielectric section further comprises an electromagnetic impedance tuner configured to vary a wall thickness of the sample holder.

10. The sensor of claim 1, wherein the composite dielectric section further comprises an electromagnetic impedance tuner configured to vary a position of the sample holder with respect to the discontinuity.

11. The sensor of claim 1, wherein the composite dielectric section further comprises an electromagnetic impedance tuner configured to vary a dimension of the discontinuity.

12. The sensor of claim 11, wherein the electromagnetic impedance tuner is a diaphragm.

13. The sensor of claim 1, wherein the composite dielectric section further comprises an electromagnetic impedance tuner, and wherein the electromagnetic impedance tuner comprises a dual chamber holder that includes a first part and a second part, wherein the first part is configured to hold the sample, and the second part is configured to hold a liquid with a tunable composition.

14. The sensor of claim 1, wherein the composite dielectric section further comprises an electromagnetic impedance tuner configured to vary dimensions of the composite dielectric section in a direction perpendicular to the propagation direction of the waveguide.

15. A method for designing a sensor according to claim 1, the method comprising:
selecting a frequency band;
dimensioning the waveguide in accordance with the selected frequency band; and
dimensioning the composite dielectric section as a quasi-half wavelength resonator within the selected frequency band.

16. The method of claim 15, wherein dimensioning the composite dielectric section comprises dimensioning at least one of the sample holder or the discontinuity.

17. A method for operating a sensor according to 1, the method comprising:
introducing a sample in the sample holder, and
measuring a response of the waveguide.

18. The method of claim 17 further comprising, before introducing the sample, calibrating the sensor by introducing a reference sample in the sample holder and tuning the sensor to thereby minimize a reflection signal at a resonance frequency of the composite dielectric section.

19. The method of claim 18 further comprising, before calibrating the sensor with the reference sample, further calibrating an electromagnetic impedance tuner of the composite dielectric section by introducing a calibration element into the sensor and tuning the sensor to thereby minimize the reflection signal at the resonance frequency, wherein the sample is a liquid.

20. A sensor for dielectric spectroscopy of a sample, the sensor comprising:
- a waveguide including a composite dielectric section, wherein the composite dielectric section comprises a sample holder and a discontinuity separating the sample holder from the waveguide,
- wherein the sample holder comprises a dual chamber holder that includes a first part and a second part, wherein the first part is configured to hold the sample, and the second part is configured to hold a liquid with a tunable composition,
- wherein an electromagnetic impedance of the composite dielectric section varies gradually, at least along a propagation direction of the waveguide, and at least from an onset of the discontinuity towards the sample holder,
- wherein the composite dielectric section has a transverse profile in a cross-section of the composite dielectric section perpendicular to the propagation direction of the waveguide,
- wherein a change in the transverse profile along the propagation direction of the waveguide causes the electromagnetic impedance to vary gradually with a tapered impedance profile, and
- wherein the composite dielectric section is arranged in the waveguide such that the waveguide extends on opposite sides of the composite dielectric section the propagation direction of the waveguide and that the waveguide at a first side of the composite dielectric section along the propagation direction of the waveguide has an electromagnetic impedance ($Z_0$) which is equal to an electromagnetic impedance ($Z_0$) of the waveguide at a second, opposite side of the composite dielectric section along the propagation direction of the waveguide.

* * * * *